United States Patent
Assmann et al.

(10) Patent No.: US 6,642,181 B2
(45) Date of Patent: Nov. 4, 2003

(54) ISOTHIAZOLE CARBOXYLIC ACID AMIDES AND THE APPLICATION THEREOF IN ORDER TO PROTECT PLANTS

(75) Inventors: Lutz Assmann, Langenfeld (DE); Dietmar Kuhnt, Burscheid (DE); Hans-Ludwig Elbe, Wuppertal (DE); Christoph Erdelen, Leichlingen (DE); Stefan Dutzmann, Langenfeld (DE); Gerd Hänssler, Leverkusen (DE); Klaus Stenzel, Düsseldorf (DE); Astrid Mauler-Machnik, Leichlingen (DE); Yoshinori Kitagawa, Moka (JP); Haruko Sawada, Yuki (JP); Haruhiko Sakuma, Oyama (JP)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/010,434

(22) Filed: Dec. 6, 2001

(65) Prior Publication Data

US 2002/0091067 A1 Jul. 11, 2002

Related U.S. Application Data

(62) Division of application No. 09/826,572, filed on Apr. 5, 2001, now Pat. No. 6,372,692, which is a division of application No. 09/530,721, filed on May 3, 2000, now Pat. No. 6,277,791.

(30) Foreign Application Priority Data

Nov. 12, 1997 (DE) .......................... 197 50 012

(51) Int. Cl.$^7$ .................. A01N 43/80; C07D 275/02; C07D 275/03
(52) U.S. Cl. ...................... 504/269; 548/214
(58) Field of Search .............. 548/214; 504/269

(56) References Cited

U.S. PATENT DOCUMENTS

| | | | |
|---|---|---|---|
| 3,341,547 A | 9/1967 | Mailey | 260/302 |
| 4,906,280 A | 3/1990 | Sandler et al. | 71/90 |
| 5,240,951 A | 8/1993 | Shimotori et al. | 514/372 |

FOREIGN PATENT DOCUMENTS

| | | | | |
|---|---|---|---|---|
| DE | 17 70 976 | | 1/1972 | |
| EP | 0 313 091 | | 4/1989 | |
| JP | 06-9313 A | * | 1/1994 | A01N/43/80 |

OTHER PUBLICATIONS

Patent Abstracts of Japan, vol. 018, No. 209 (C–1190), Apr. 13, 1994, & JP 06 009313 A (Mitsui Toatsu Chem. Inc.), Jan. 18, 1994, in der Anmeldung erwähnt siehe Zusammenfassung; Beispiele 25,26,36–38.

* cited by examiner

*Primary Examiner*—Laura L. Stockton
(74) *Attorney, Agent, or Firm*—Joseph C. Gil; Richard E. L. Henderson; Raymond J. Harmuth

(57) ABSTRACT

Novel isothiazolecarboxamides of the formula

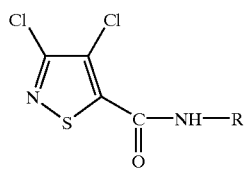

(I)

in which

R is as defined in the description, a plurality of processes for preparing the novel compounds and their use for protecting plants against attack by undesirable microorganisms and animal pests.

5 Claims, No Drawings

ISOTHIAZOLE CARBOXYLIC ACID AMIDES AND THE APPLICATION THEREOF IN ORDER TO PROTECT PLANTS

This is a Divisional application of Ser. No. 09/826,572 filed Apr. 5, 2001, U.S. Pat. No. 6,372,692, which in turn was a Divisional application of Ser. No. 09/530,721, filed May 3, 2000, now U.S. Pat. No. 6,277,791.

The present invention relates to novel isothiazolecarboxamides, to a plurality of processes for their preparation and to their use for protecting plants against attack by undesirable microorganisms and animal pests.

It is already known that numerous isothiazolecarboxylic acid derivatives have fungicidal properties (cf. U.S. Pat. No. 5,240,951 and JP-A 06-009 313). Thus, for example, N-ethyl-3,4-dichloro-isothiazole-5-carboxamide and 3,4,4'-trichloro-isothiazole-5-carboxanilide can be employed for controlling fungi. The activity of these compounds is good, but in some cases leaves something to be desired at low application rates.

This invention, accordingly, provides novel isothiazole-carboxamides of the formula

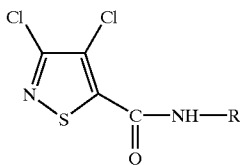

(I)

in which
R represents a radical of the formula

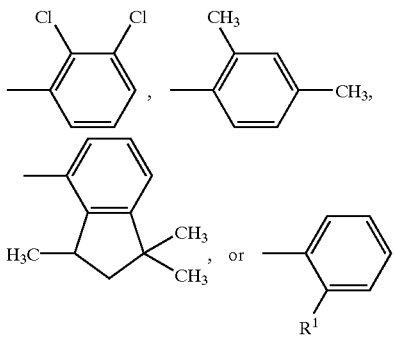

in which
$R^1$ represents cyano, phenyl or cycloalkyl having 3 to 7 carbon atoms,
or
R represents a radical of the formula

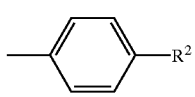

in which
$R^2$ represents —C(CH$_3$)$_3$,

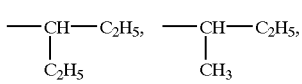

cycloalkyl having 3 to 7 carbon atoms or represents —CH$_2$—S—R$^3$, where
$R^3$ represents alkyl having 1 to 6 carbon atoms or represents phenyl which is optionally substituted by halogen and/or alkyl having 1 to 6 carbon atoms,
or
R represents a radical of the formula

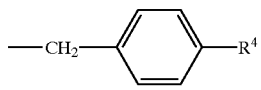

in which
$R^4$ represents hydrogen or N,N-dialkylaminomethyl having 1 to 4 carbon atoms in each alkyl moiety,
or
R represents a radical of the formula

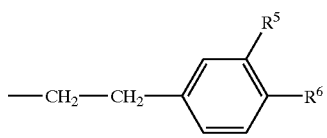

in which
$R^5$ represents hydrogen or alkoxy having 1 to 4 carbon atoms and
$R^6$ represents alkoxy having 1 to 4 carbon atoms, alkyl having 1 to 6 carbon atoms, optionally halogen-substituted phenyl or represents optionally halogen-substituted phenoxy,
or
$R^5$ represents optionally halogen-substituted phenoxy and
$R^6$ represents hydrogen,
or
R represents a radical of the formula

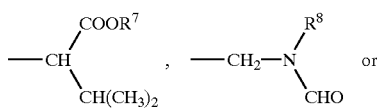

—CH$_2$—CH$_2$—O—R$^9$ in which
$R^7$ represents alkyl having 1 to 4 carbon atoms,
$R^8$ represents alkyl having 1 to 4 carbon atoms, and
$R^9$ represents hydrogen or a radical of the formula

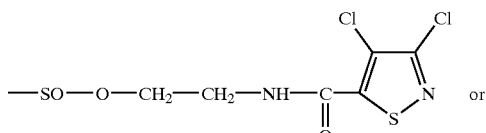

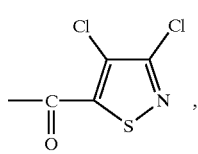

or

R represents a radical of the formula

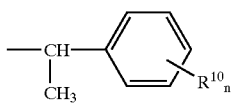

in which
R$^{10}$ represents halogen, alkyl having 1 to 4 carbon atoms or alkoxy having 1 to 4 carbon atoms and
n represents integers from 0 to 3.

Furthermore, it has been found that isothiazolecarboxamides of the formula (I) are obtained when a) 3,4-dichloro-isothiazole-5-carbonyl chloride of the formula

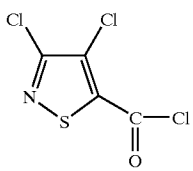
(II)

is reacted with amines of the formula

  (III)

in which
R is as defined above,
if appropriate in the presence of an acid binder and if appropriate in the presence of a diluent,
or b) 3,4-dichloro-isothiazole-5-carboxamide of the formula

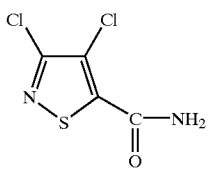
(IV)

is reacted with hydroxyl compounds of the formula

HO—CH$_2$—X  (V)

in which
X represents a radical of the formula

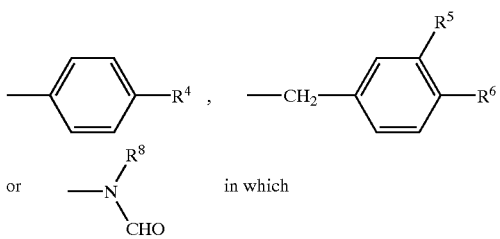

R$^4$, R$^5$, R$^6$ and R$^8$ are each as defined above,
in the presence of a diluent and in the presence of a dehydrating agent.

Finally, it has been found that the isothiazolecarboxamides of the formula (I) are highly suitable for protecting plants against attack by undesirable microorganisms. The compounds according to the invention are suitable both for mobilizing defences of the plants against attack by undesirable microorganisms and as microbicides for the direct control of the microorganisms. Additionally, the compounds according to the invention also exhibit activity against plant-damaging animals.

Surprisingly, the compounds according to the invention have better microbicidal activity than N-ethyl-3,4-dichloroisothiazole-5-carboxamide and 3,4,4'-trichloro-isothiazole-5-carboxanilide, which are constitutionally similar prior-art active compounds of the same direction of action.

The formula (I) provides a general definition of the isothiazolecarboxamides according to the invention. Preference is given to compounds of the formula (I) in which
R represents a radical of the formula

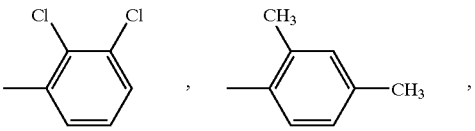

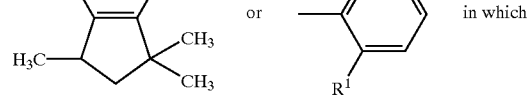

R$^1$ represents cyano, phenyl, cyclopentyl, cyclohexyl or cycloheptyl,
or
R represents a radical of the formula

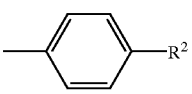

in which
R$^2$ represents —C(CH$_3$)$_3$,

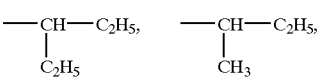

cyclopentyl, cyclohexyl, cycloheptyl or represents —CH$_2$—S—R$^3$ where
R$^3$ represents alkyl having 1 to 5 carbon atoms or represents phenyl which is optionally mono- to trisubstituted by identical or different constituents selected from the group consisting of fluorine, chlorine, bromine and alkyl having 1 to 4 carbon atoms,
or
R represents a radical of the formula

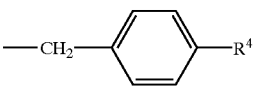

in which
R$^4$ represents hydrogen or N,N-dialkyl-aminomethyl having 1 or 2 carbon atoms in each alkyl moiety,
or R represents a radical of the formula

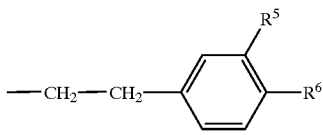

in which
- $R^5$ represents hydrogen or alkoxy having 1 or 2 carbon atoms and
- $R^6$ represents alkoxy having 1 or 2 carbon atoms, alkyl having 1 to 4 carbon atoms, phenyl which is optionally mono- to trisubstituted by identical or different substituents selected from the group consisting of fluorine, chlorine and bromine or represents phenoxy which is optionally mono- to trisubstituted by identical or different substituents selected from the group consisting of fluorine, chlorine and bromine, or
- $R^5$ represents phenoxy which is optionally mono- to trisubstituted by identical or different substituents selected from the group consisting of fluorine, chlorine and bromine and
- $R^6$ represents hydrogen, or
R represents a radical of the formula

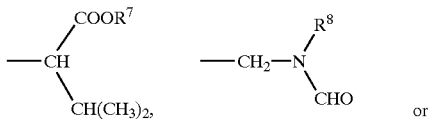

—$CH_2$—$CH_2$—O—$R^9$ in which
- $R^7$ represents methyl or ethyl,
- $R^8$ represents methyl or ethyl and
- $R^9$ represents hydrogen or a radical of the formula

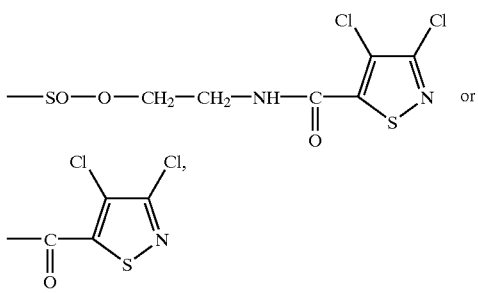

or
R represents a radical of the formula

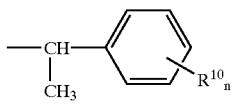

in which
- $R^{10}$ represents fluorine, chlorine, bromine, methyl, ethyl, methoxy or ethoxy and
- n represents integers from 0 to 3, where $R^{10}$ represents identical or different radicals if n represents 2 or 3.

The abovementioned substituent definitions can be combined among each other. Additionally, individual definitions may be redundant.

Using 3,4-dichloro-isothiazole-5-carbonyl chloride and 2-cyanoaniline as starting materials, the course of the process (a) according to the invention can be illustrated by the equation below.

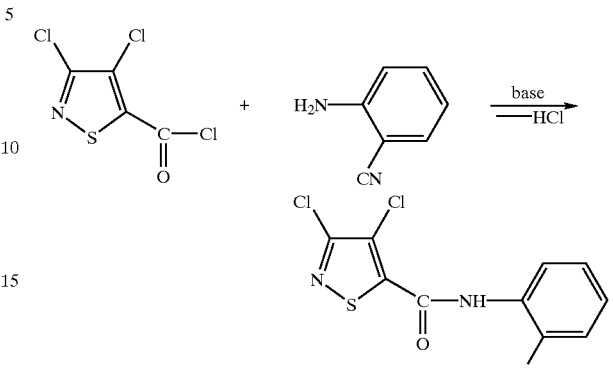

Using 3,4-dichloro-isothiazole-5-carboxamide and N-formyl-N-hydroxy-methyl-methylamine as starting materials, the course of the process (b) according to the invention can be illustrated by the equation below.

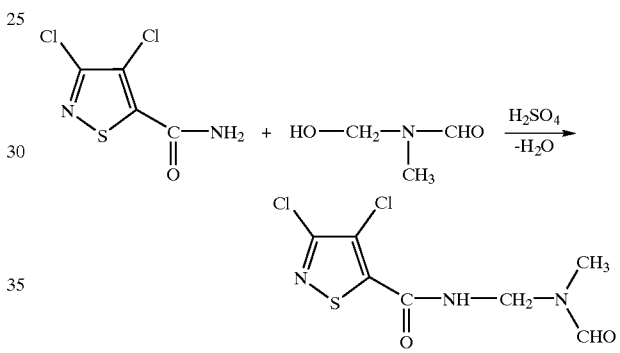

The 3,4-dichloro-isothiazole-5-carbonyl chloride of the formula (II) required as starting material for carrying out the process (a) according to the invention is known (cf. U.S. Pat. No. 5,240,951).

The formula (III) provides a general definition of the amines furthermore required as reaction components for carrying out the process (a) according to the invention. In this formula, R preferably has those meanings which have already been mentioned in connection with the description of the compounds of the formula (I) according to the invention as being preferred for this radical.

The amines of the formula (III) are known or can be prepared by known methods.

Suitable acid binders for carrying out the process (a) according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate, furthermore ammonium hydroxide, ammonium acetate or ammonium carbonate, or tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (a) according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichlorethane or trichloroethane; ethers, such as diethyl ether, diisopropyl ether, methyl-t-butyl ether, methyl-t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric acid triamide; esters such as methyl acetate or ethyl acetate; sulphoxides, such as dimethylsulphoxide; sulphones, such as sulpholane.

When carrying out the process (a) according to the invention the reaction temperatures can be varied within a relatively wide range. In general, the reaction is carried out at temperatures between −10° C. and +150° C., preferably between 0° C. and 100° C.

The process (a) according to the invention is generally carried out under atmospheric pressure. However, it is also possible to operate under elevated or, if no volatile components take part in the reaction, under reduced pressure.

When carrying out the process (a) according to the invention, generally 1 to 5 mol, preferably 1 to 2 mol, of amine of the formula (III) and an equivalent amount or an excess of acid binder are employed per mole of 3,4-dichloro-isothiazole-5-carbonyl chloride of the formula (II). Work-up is carried out by customary methods. In general, the reaction mixture is concentrated after the reaction has ended, the residue that remains is admixed with water and an organic solvent which is sparingly miscible with water, the organic phase is separated off, washed, dried and concentrated. The product that remains can be freed of any impurities that may be present by customary methods.

The 3,4-dichloro-isothiazole-5-carboxamide of the formula (IV) required as starting material for carrying out the process (b) according to the invention is known (cf. U.S. Pat. No. 5,240,951).

The formula (V) provides a general definition of the hydroxyl compounds furthermore required as reaction components for carrying out the process (b) according to the invention. In this formula X preferably represents a radical of the formula

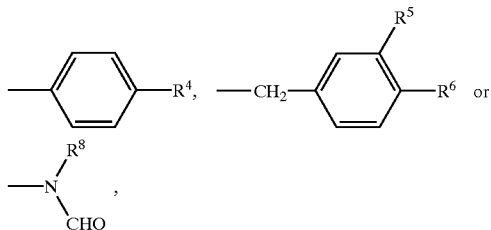

in which
R$^4$ represents hydrogen or N,N-dialkyl-aminomethyl having 1 or 2 carbon atoms in each alkyl moiety,
R$^5$ represents hydrogen or alkoxy having 1 or 2 carbon atoms,
R$^6$ represents alkoxy having 1 or 2 carbon atoms, alkyl having 1 to 4 carbon atoms, phenyl which is optionally mono- to trisubstituted by identical or different substituents selected from the group consisting of fluorine, chlorine and bromine or represents phenoxy which is optionally mono- to trisubstituted by identical or different substituents selected from the group consisting of fluorine, chlorine and bromine,
or
R$^5$ represents phenoxy which is optionally mono- to trisubstituted by identical or different substituents selected from the group consisting of fluorine, chlorine and bromine and
R$^6$ represents hydrogen and
R$^8$ represents methyl or ethyl.

The hydroxyl compounds of the formula (V) are known or can be prepared by known methods.

Suitable diluents for carrying out the process (b) according to the invention are all inert organic solvents which are customary for such reactions. Preference is given to using glacial acetic acid.

Suitable dehydrating agents for carrying out the process (b) according to the invention are all customary reagents which are capable of dehydration. Preference is giving to using acids, such as sulphuric acid or p-toluenesulphonic acid, and also drying agents, such as anhydrous silica gel.

When carrying out the process (b) according to the invention, the reaction temperatures can again be varied within a relatively wide range. In general, the reaction is carried out at temperatures between 0° C. and 150° C., preferably between 10° C. and 130° C.

The process (b) according to the invention is likewise generally carried out under atmospheric pressure. However, it is also possible to carry out the process under elevated or reduced pressure.

When carrying out the process (b) according to the invention, generally 1 to 2 mol, preferably 1 to 1.5 mol, of hydroxyl compound of formula (V) and 2 to 6 mol of dehydrating agent are employed per mole of 3,4-dichloro-isothiazole-5-carboxamide of the formula (IV). Work-up is carried out by customary methods. In general, the reaction mixture is admixed with water and then extracted with an organic solvent which is sparingly miscible with water, and the combined organic phases are dried and concentrated under reduced pressure. The product that remains can be freed of any impurities that may still be present by customary methods.

The active compounds according to the invention have a strong plant-strengthening activity in plants. They are therefore suitable for mobilizing the defences of the plant against attack by undesirable microorganisms.

In the present context, plant-strengthening (resistance-inducing) compounds are compounds which are capable of stimulating the defensive system of plants in such a way that the treated plants, when subsequently inoculated with undesirable microorganisms, develop substantial resistance against these microorganisms.

In the present case, undesirable microorganisms are phytopathogenic fungi, bacteria and viruses. The compounds according to the invention can thus be employed to protect plants for a certain period of time after the treatment against the attack by the abovementioned harmful organisms. The period of time for which protection is provided generally extends from 1 to 10 days, preferably from 1 to 7 days, after the treatment of the plants with the active compounds.

In addition to the plant-strengthening (resistance-inducing) activity, the active compounds according to the invention also have strong microbicidal activity and are additionally employed in practice for the direct control of undesirable microorganisms.

The active compounds are suitable for use as crop protection agents, in particular as fungicides.

In crop protection, the undesirable microorganisms include fungi from the classes of the Plasmodiophoromycetes, Oomycetes, Chytridiomycetes, Zygomycetes, Ascomycetes, Basidiomycetes, Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidia form: Drechslera, syn.: Helminthosporium);

Cochliobolus species, such as, for example, *Cochliobolus sativus* (conidia form: Drechslera, syn.: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The good crop safety of the active compounds at the concentrations necessary for controlling plant diseases permits a treatment of above-ground parts of plants, and also a treatment of vegetative propagation stock and seed and of the soil.

The active compounds according to the invention can be used here particularly successfully for controlling cereal diseases, such as, for example, against Erysiphe species, or of diseases in viticulture and in fruit and vegetable growing, such as, for example, against Plasmopara or Venturia species, or of rice diseases, such as, for example, against Pyricularia species. Other plant diseases, such as, for example, Septoria, Cochliobolus, Pyrenophora and Pseudocercosporella species, can also be controlled successfully with the active compounds according to the invnetion, and specific mention may be made of *Drechslera teres.*

The active compounds according to the invention are also suitable for increasing the harvest yield. Additionally, they have reduced toxicity and good crop safety.

The active compounds which can be employed according to the invention, having good crop tolerance and homeotherm safety, are also suitable for controlling animal pests, in particular insects, arachnids and nematodes, which are encountered in agriculture, in forests, in horticulture, in the protection of stored products and of materials, and in the hygiene sector and in veterinary medicine. They are active against normally sensitive and resistant species and against pests in all or some stages of development. The abovementioned animal pests include:

From the order of Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophorai gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,*

Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds which can be used according to the invention can be employed particularly successfully for controlling plant-damaging mites, such as against the greenhouse red spider mite (*Tetranychus urticae*) or for controlling plant-damaging insects, such as against the caterpillars of the diamond-back moth (*Plutella maculipennis*), the larvae of the mustard beetle (*Phaedon cochleariae*), and also the green rice leaf hopper (*Nephotettix cincticeps*).

The compounds according to the invention additionally have herbicidal activity.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuiram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, flirmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolini, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1, 2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methylcyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d] pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propinyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5] decane-2-methaneamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethylmorpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one.

Bactericides:
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethaneimidamide, chlorpyrifos, chlorpyrifos M, cis-resmethirin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenoplhos, hexaflumuron, hexythiazox, imidacloprid, iprobenfos, isazophos, isofenphos, isoprocarb, isoxathion, ivermectin, lambda-cyalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, pernethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, or else fertilizers and growth-promoting substances.

The active compounds can be used as such, in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When using the active compounds according to the invention for controlling microorganisms, the application rates can be varied within a relatively wide range, depending on the kind of application. When treating parts of plants, the active compound application rates are generally between 0.1 and 10,000 g/ha, preferably between 10 and 1000 g/ha. When treating seed, the active compound application rates are generally between 0.001 and 50 g per kilogram of seed, preferably between 0.01 and 10 g per kilogram of seed. When treating the soil, the active compound application rates are generally between 0.1 and 10,000 g/ha, preferably between 1 and 5000 g/ha.

When used against animal pests, the compounds according to the invention may also be present in commercial formulations and in the use forms prepared from these formulations as a mixture with synergists. Synergists are compounds which increase the activity of the active compounds, without it being necessary for the synergist which is added to be active itself.

The active compound content of the use forms prepared from the commercial formulations can vary within wide ranges. The active compound concentration of the use form may be from 0.0000001 to 95% by weight of active compound, preferably between 0.0001 and 1% by weight.

Application is carried out in a manner adapted to the use forms.

The preparation and the use of the active compounds according to the invention is illustrated by the examples below.

PREPARATION EXAMPLES

Example 1

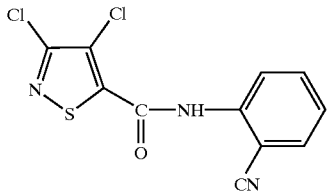

At 5 to 10° C. and with stirring, 38.1 g (0.15 mol) of 3,4-dichloro-isothiazole-5-carbonyl chloride are added dropwise over a period of 10 minutes to a mixture of 20.8 g (0.1725 mol) of 2-cyano-aniline and 250 ml of pyridine. After the addition, the reaction mixture is admixed with 70 ml of absolute tetrahydrofuran and 30 ml of pyridine, allowed to warm to room temperature and then stirred at room temperature for 75 minutes. The reaction mixture is subsequently concentrated under reduced pressure. The residue that remains is stirred with 800 ml of water and 800 ml of ethyl acetate. The precipitate which is present in the two-phase mixture is filtered off, washed with ethyl acetate and dried. This gives 31.7 g of a crystalline product of melting point 191 to 193° C.

The aqueous phase of the two-phase filtrate is separated off and extracted twice with 150 ml of ethyl acetate each time. The combined organic phases are dried over sodium sulphate and then concentrated under reduced pressure. The residue that remains is stirred with 100 ml of petroleum ether and 25 ml of ethyl acetate. The resulting solid is filtered off with suction, rinsed with ethyl acetate and dried.

In this manner, a total of 40 g (89% of theory) of 2'-cyano-3,4-dichloro-isothiazole-5-carboxamide are obtained in the form of a solid substance of melting point 191 to 193° C.

Preparation of the Starting Material:

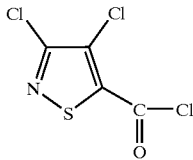

At room temperature, 146 g (1.23 mol) of thionyl chloride are added dropwise with stirring over a period of 5 minutes to 8.92 g (0.045 mol) of 3,4-dichloro-isothiazole-5-carboxylic acid. Four drops of dimethylformamide are then added and the reaction mixture is heated under reflux for one hour. The reaction mixture is subsequently cooled to room temperature and concentrated under reduced pressure. In this manner, 12.19 g of 3,4-dichloro-isothiazole-5-carbonyl chloride are obtained in the form of an orange oil.

Example 2

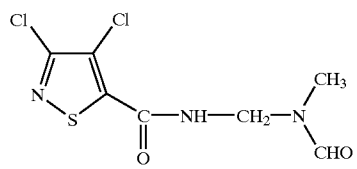

At room temperature, 15 g (0.164 mol) of N-formyl-N-hydroxymethyl-methylamine are added with stirring to a mixture of 32.3 g (0.164 mol) of 3,4-dichloro-isothiazole-5-carboxamide and 245 ml of glacial acetic acid. At room temperature, 37 g (0.362 mol) of concentrated sulphuric acid are then added dropwise with stirring, the reaction mixture being cooled with ice. The reaction mixture is subsequently stirred at room temperature for 29 hours and then, with ice-cooling, admixed with 400 ml of water. The resulting mixture is extracted four times with 200 ml of methylene chloride and the combined organic phases are dried over sodium sulphate and then concentrated under reduced pressure. The oily residue that remains is chromatographed over silica gel using ethyl acetate. Concentration of the eluate gives 20.7 g (42.6% of theory) of N-(N-formyl-N-methyl-aminomethyl)-3,4-dichloroisothiazole-5-carboxamide in the form of a crystalline solid of melting point 87 to 88° C.

Preparation of the Starting Material

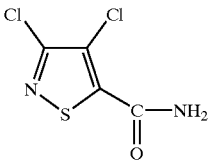

At 0 to 10° C., 50.1 g (0.2 mol) of 3,4-dichloro-isothiazole-5-carbonyl chloride are added dropwise with stirring over a period of 30 minutes to 82 g (1.2 mol) of concentrated ammonia. After the addition, another 41 g (0.6 mol) of concentrated ammonia are added and the mixture is diluted with 70 ml of water. The mixture is allowed to warm to room temperature and stirred at this temperature for 45 minutes. The resulting precipitate is filtered off with suction, washed successive with water and petroleum ether and dried. In this manner, 32.3 g (81.8% of theory) of 3,4-dichloro-isothiazole-5-carboxamide are obtained in the form of a solid of melting point 156 to 158° C.

The compounds of the formula (I) listed in the Table below are also prepared by the abovementioned methods.

TABLE 1

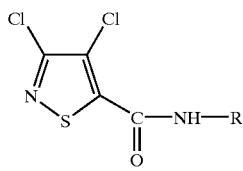

(I)

| Example No. | R | Physical Constants |
|---|---|---|
| 3 | 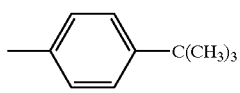 | m.p. 148–149° C. |

TABLE 1-continued (I)

Structure: 3,4-dichloroisothiazole-5-carboxamide with N-R substituent

| Example No. | R | Physical Constants |
|---|---|---|
| 4 | —CH₂—CH₂—C₆H₄—C(CH₃)₃ | log P = 4.81*); λ = 218, 244 and 266 nm**) |
| 5 | —CH₂—CH₂—C₆H₄—O—C₆H₄—Cl | log P = 4.86; λ = 234 and 270 nm |
| 6 | —CH₂—CH₂—C₆H₄—O—C₆H₄—Cl | log p = 4.79; λ = 232 and 270 nm |
| 7 | —CH(COOCH₃)—CH(CH₃)₂ | log P = 3.15; λ = 242 and 266 nm |
| 8 | —CH₂—C₆H₅ | m.p. = 91–92° C. |
| 9 | —C₆H₃(CH₃)₂ (2,4-dimethylphenyl) | m.p. = 171–172° C. |
| 10 | —CH₂—CH₂—O—SO—O—(CH₂)₂—NH—C(O)—(3,4-dichloroisothiazol-5-yl) | m.p. = 70–75° C. |
| 11 | —CH₂—CH₂—OH | m.p. = 115–117° C. |
| 12 | —C₆H₄—CH₂—S—C₆H₄—C(CH₃)₃ | m.p. = 126–128° C. |
| 13 | —C₆H₄—CH₂—S—CH₂—C(CH₃)₃ | m.p. = 91–92° C. |
| 14 | —CH₂—C₆H₄—CH₂—N(C₂H₅)₂ | log P = 1.39; λ = 219 and 243 nm |
| 15 | —C₆H₄—CH(C₂H₅)₂ | m.p. = 98–99° C. |

TABLE 1-continued
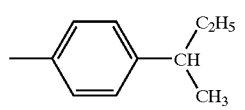
(I)
| Example No. | R | Physical Constants |
|---|---|---|
| 16 | 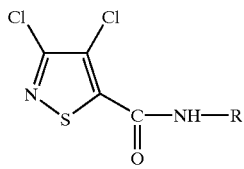 | m.p. = 83–85° C. |
| 17 | 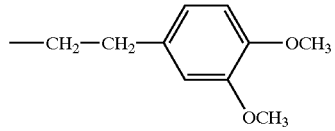 | m.p. = 81–83° C. |
| 18 | 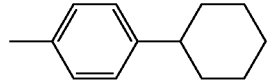 | m.p. = 162–163° C. |
| 19 | 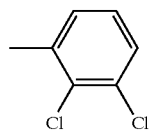 | m.p. = 196° C. |
| 20 | 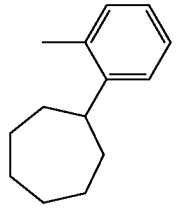 | m.p. = 122–125° C. |
| 21 | 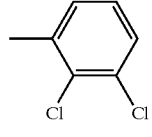 | m.p. = 83–84° C. (Decomp.) |
| 22 | 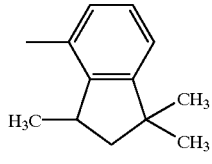 | m.p. = 129–130° C. |
| 23 | 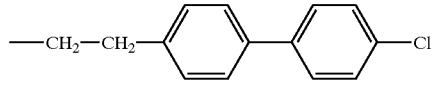 | m.p. = 135–136° C. |
| 24 | 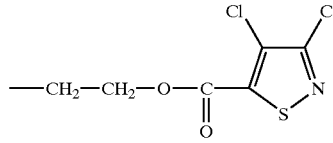 | m.p. = 88–89° C. |

TABLE 1-continued

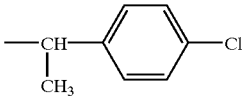

| Example No. | R | Physical Constants |
|---|---|---|
| 25 | —CH(CH₃)—C₆H₄—Cl | m.p. = 89–90° C. |

*) The log P values were determined in accordance with EEC Directive 79/831 Annex V. A8 by HPLC (Gradient method, acetonitrile/0.1% aqueous phosphoric acid).
**) The λ values denote maxima in the UV spectrum.

USE EXAMPLES

Example A
Pyricularia Test (Rice)/Induction of Resistance

| Solvent: | 2.5 parts by weight of acetone |
|---|---|
| Emulsifier: | 0.06 parts by weight of alkylaryl polyglycol ether |

To produce a suitable preparation of active compound, 1 part by weight of active compound is mixed with the stated amount of solvent, and the concentrate is diluted with water and the stated amount of emulsifer to the desired concentration.

To test for resistance-reducing activity, young rice plants are sprayed with the preparation of active compound at the stated application rate. 5 days after the treatment, the plants are inoculated with an aqueous spore suspension of *Pyricularia oryzae*. The plants are subsequently placed in a greenhouse at 100% relative atmospheric humidity and a temperature of 25° C.

Evaluation is carried out 4 days after the inoculation. 0% means an efficacy which corresponds to that of the control, while an efficacy of 100% means that no infection is observed.

Active compounds, application rates and tests results are shown in the Table below.

TABLE A

Pyricularia Test (Rice)/Induction of resistance

| Active compound | Application rate of active compound in g/ha | Efficacy in % |
|---|---|---|
| According to the invention: | | |
| 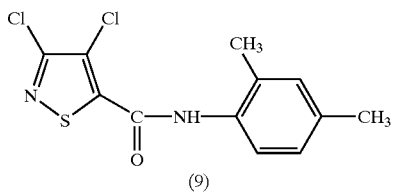 (9) | 750 | 90 |
| 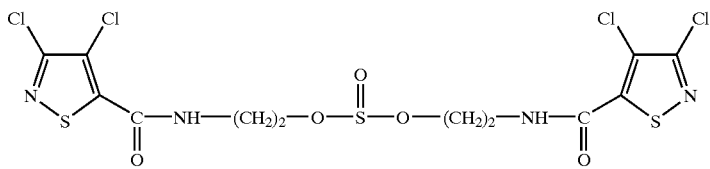 (10) | 750 | 90 |

TABLE A-continued

Pyricularia Test (Rice)/Induction of resistance

| Active compound | Application rate of active compound in g/ha | Efficacy in % |
|---|---|---|
| 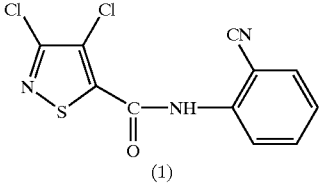 (1) | 750 | 90 |
| 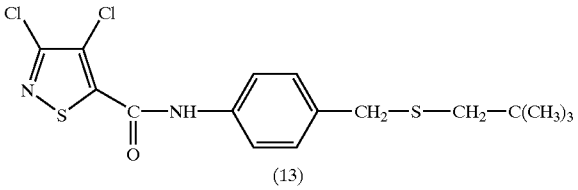 (13) | 750 | 90 |
| 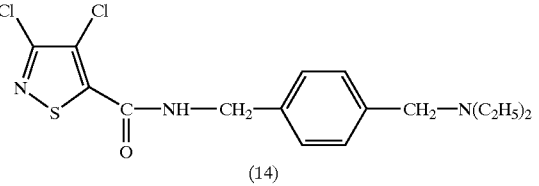 (14) | 750 | 100 |
| 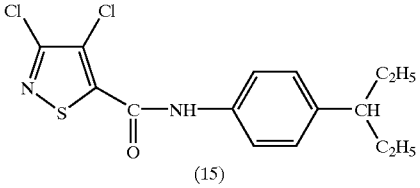 (15) | 750 | 90 |
| 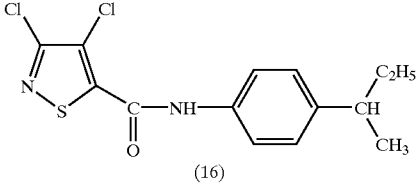 (16) | 750 | 90 |

Example B

Phaedon Larvae Test

| | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and populated with larvae of the mustard beetle (*Phaedon cochleariae*) while the leaves are still moist.

After 7 days, the kill is determined and expressed in percent. An efficacy of 100% means that all beetle larvae have been killed, while an efficacy of 0% means that no beetle larvae have been killed.

Active compounds, active compound concentrations and test results are shown in the Table below.

TABLE B

Phaedon Larvae Test/plant-damaging insects

| Active compound | Concentration of active compound in % by weight | Kill in % after 7 d |
|---|---|---|
| 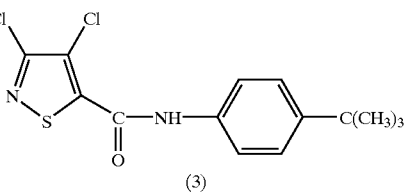 (3) | 0.1 | 100 |

Example C

Plutella Test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and populated with caterpillars of the diamond-back moth (*Plutella xylostella*) while the leaves are still moist.

After 7 days, the kill is determined and expressed in percent. An efficacy of 100% means that all caterpillars have been killed, while an efficacy of 0% means that none of the caterpillars have been killed.

Active compounds, active compound concentrations and test results are shown in the Table below.

TABLE C

Plutella Test/plant-damaging insects

| Active compound | Concentration of active compound in % by weight | Kill in % after 7 d |
|---|---|---|
| 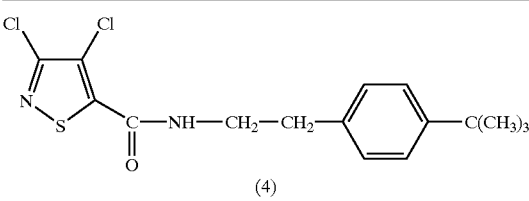 (4) | 0.1 | 100 |
| 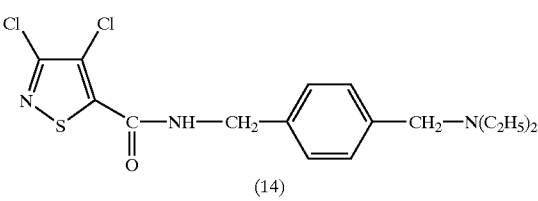 (14) | 0.1 | 100 |
| 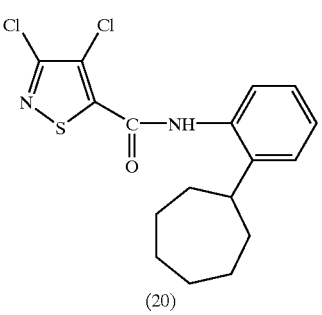 (20) | 0.1 | 100 |

TABLE C-continued

Plutella Test/plant-damaging insects

| Active compound | Concentration of active compound in % by weight | Kill in % after 7 d |
|---|---|---|
| (21) 3,4-dichloro-isothiazole-5-carboxamide of 2-aminobiphenyl | 0.1 | 100 |
| (23) 3,4-dichloro-isothiazole-5-carboxamide of 2-(4'-chloro-biphenyl-4-yl)ethylamine | 0.1 | 100 |

Example D
Venturia Test (Apple)/Protective

| Solvent: | 47 parts by weight of acetone |
|---|---|
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab Venturia inaequalis and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, while an efficacy of 100% means that no infection is observed.

Active compounds, application rates and test results are shown in the Table below.

TABLE D

Venturia Test (Apple)/protective

| Active compound | Application rate of active compound in g/ha | Efficacy in % |
|---|---|---|
| According to the invention: | | |
| (6) 3,4-dichloro-isothiazole-5-carboxamide of 2-[3-(4-chlorophenoxy)phenyl]ethylamine | 100 | 96 |

Example E

*Leptosphaeria nodorum* Test (Wheat)/Protective

| | |
|---|---|
| Solvent: | 10 parts by weight of N-methyl-pyrrolidone |
| Emulsifier: | 0.6 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relative atmospheric humidity for 48 hours.

The plants are then placed in a greenhouse at a temperature of approximately 15° C. and a relative atmospheric humidity of 80%.

Evaluation is carried out 10 days after the inoculation. 0% means an efficacy which corresponds to that of the control, while an efficacy of 100% means that no infection is observed.

Active compounds, application rates and test results are shown in the Table below.

TABLE E

Leptosphaeria nodorum Test (Wheat)/protective

| Active compound | Application rate of active compound in g/ha | Efficacy in % |
|---|---|---|
| According to the invention: | | |
| 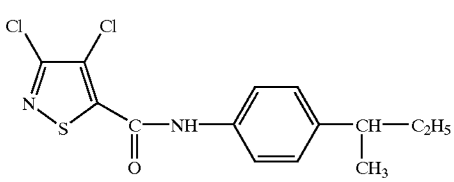  (16) | 250 | 81 |

What is claimed is:

1. An isothiazolecarboxamide of the formula (I)

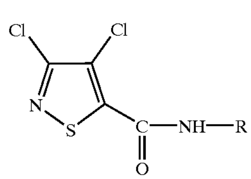

in which

R represents a radical of the formula 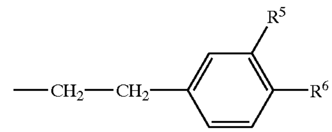 in which $R^5$ represents hydrogen or alkoxy having 1 to 4 carbon atoms and $R^6$ represents alkoxy having 1 to 4 carbon atoms, alkyl having 1 to 6 carbon atoms, optionally halogen-substituted phenyl or represents optionally halogen-substituted phenoxy, or $R^5$ represents optionally halogen-substituted phenoxy and $R^6$ represents hydrogen.

2. A process for preparing an isothiazolecarboxamide of the formula (I) according to claim 1 comprising the steps of a) reacting 3,4-dichloro-isothiazole-5-carbonyl chloride of the formula (II)

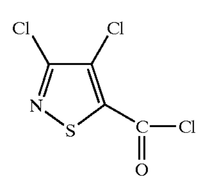

with an amine of the formula $H_2N—R$ (III)

in which
R is as defined in claim 1, or b) reacting 3,4-dichloro-isothiazole-5-carboxamide of the formula

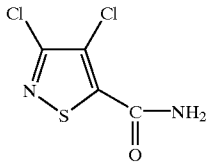 (IV)

with a hydroxyl compound of the formula

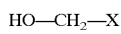 (V)

in which
X represents a radical of the formula

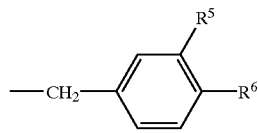

in which
$R^5$ and $R^6$ are each as defined in claim 1, in the presence of a diluent and in the presence of a dehydrating agent.

3. A fungicidal composition comprising an effective amount of at least one isothiazole-carboxamide of the formula (I) according to claim 1 and an extender and/or a surfactant.

4. A method for controlling fungi comprising applying an effective amount of an isothiazole-carboxamide of the formula (I) according to claim 1 to one or more plants and/or their habitat.

5. An isothiazolecarboxamide, wherein said isothiazole-carboxamide is represented by the formula:

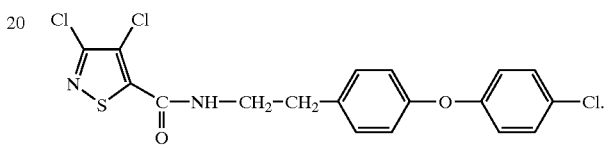

* * * * *